(12) United States Patent
Bar-Shalev (10) Patent No.: US 8,391,578 B2
(45) Date of Patent: Mar. 5, 2013

(54) METHOD AND APPARATUS FOR AUTOMATICALLY REGISTERING IMAGES

(75) Inventor: Avi Bar-Shalev, Kiryat Haim (IL)

(73) Assignee: General Electric Company, Schenectady, NY (US)

( * ) Notice: Subject to any disclaimer, the term of this patent is extended or adjusted under 35 U.S.C. 154(b) by 670 days.

(21) Appl. No.: 12/616,429

(22) Filed: Nov. 11, 2009

(65) Prior Publication Data

US 2011/0110571 A1     May 12, 2011

(51) Int. Cl.
*G06K 9/62*     (2006.01)
(52) U.S. Cl. ........................................ 382/131
(58) Field of Classification Search ............... 382/128, 382/131, 132, 159, 294, 173; 600/410, 434, 600/407, 523
See application file for complete search history.

(56) References Cited

U.S. PATENT DOCUMENTS

| | | | |
|---|---|---|---|
| 5,871,013 A | 2/1999 | Wainer et al. | |
| 5,974,165 A * | 10/1999 | Giger et al. | 382/132 |
| 6,292,683 B1 * | 9/2001 | Gupta et al. | 600/410 |
| 6,841,782 B1 | 1/2005 | Balan et al. | |
| 6,878,941 B2 | 4/2005 | Balan et al. | |
| 7,087,903 B2 | 8/2006 | Balan et al. | |
| 7,110,587 B1 | 9/2006 | Natanzon et al. | |
| 7,194,062 B2 | 3/2007 | Balan et al. | |
| 7,907,759 B2 * | 3/2011 | Hundley et al. | 382/128 |
| 7,912,270 B2 * | 3/2011 | Skinner et al. | 382/131 |
| 2006/0093209 A1 * | 5/2006 | Guetter et al. | 382/159 |
| 2006/0116575 A1 * | 6/2006 | Willis | 600/434 |
| 2006/0239524 A1 * | 10/2006 | Desh et al. | 382/128 |
| 2007/0036418 A1 * | 2/2007 | Pan et al. | 382/131 |
| 2007/0047840 A1 * | 3/2007 | Xu et al. | 382/294 |
| 2007/0165923 A1 * | 7/2007 | Shen et al. | 382/128 |
| 2007/0196007 A1 * | 8/2007 | Chen et al. | 382/131 |
| 2007/0223794 A1 * | 9/2007 | Preiss et al. | 382/128 |
| 2007/0274582 A1 * | 11/2007 | Yatziv et al. | 382/131 |

OTHER PUBLICATIONS

Guido Germano et al., A New Algorithm for the Quantification of Myocardial Perfusion SPECT.I: Technical Principles and Reproducibility, The Journal of Nuclear Medicine, vol. 41, No. 4, Apr. 2000, pp. 712-719.

* cited by examiner

*Primary Examiner* — Lena Najarian
*Assistant Examiner* — Natalie A Pass
(74) *Attorney, Agent, or Firm* — The Small Patent Law Group; Dean D. Small (57) ABSTRACT

Methods and apparatus for automatically registering an anatomical image with a perfusion image is provided. The method includes acquiring an anatomical image of a heart using a first imaging modality, acquiring a physiological image of the heart using a different second imaging modality, identifying a myocardium of a left ventricle using the physiological image, automatically scoring a plurality of pixels in the anatomical image that are within a predetermined range of the myocardium identified in the physiological image, and registering the anatomical image with the physiological image based on the score.

19 Claims, 5 Drawing Sheets

METHOD AND APPARATUS FOR AUTOMATICALLY REGISTERING IMAGES

BACKGROUND OF THE INVENTION

The subject matter disclosed herein relates generally to medical imaging systems and, more particularly, to an apparatus and method for automatically registering images of the heart acquired by different medical imaging modalities.

Single Photon Emission Computed Tomography (SPECT) imaging systems and Positron Emission Tomography (PET) imaging systems generally acquire images showing physiologic data based on the detection of radiation from the emission of photons. Images acquired using SPECT and/or PET may be used to evaluate different conditions and diseases that affect the heart or lungs, for example.

SPECT and PET scans are increasingly being used in connection with other types of medical scans, including, for example, with Computed Tomography (CT) scans. The combination of the images from the scans, often referred to as co-registration, provides both anatomic and physiological information on a single image. Combination or multimodality imaging systems are also available to perform both scans during the same scanning session. However, during the scanning procedure the patient may move or the table may sag. As a result, the images acquired, for example, from the SPECT system may not be properly registered with images acquired from the CT system. Moreover, anatomical structures, such as neighboring chest bones and lungs, each having different densities, may cause significant changes in the resultant registered image.

One conventional method of registering images includes manually identifying a specific region or landmark in both the PET image and the CT image and then aligning both sets of images based on the identified landmark. However, the above described registration method requires an operator to manually shift one image with respect to a second image. Manually registering images is time consuming, may result in operator error, and may also not properly account for motion of either the heart or the patient during the imaging procedure.

BRIEF DESCRIPTION OF THE INVENTION

In one embodiment, a method for automatically registering an anatomical image with a perfusion image is provided. The method includes acquiring an anatomical image of a heart using a first imaging modality, acquiring a physiological image of the heart using a different second imaging modality, identifying a myocardium of a left ventricle using the physiological image, automatically scoring a plurality of pixels in the anatomical image that are within a predetermined range of the myocardium identified in the physiological image, and registering the anatomical image with the physiological image based on the score.

In another embodiment, a multi-modality imaging system is provided. The multi-modality imaging system includes a first modality unit, a second modality unit, and an image registration module operationally coupled to the first and second modality units. The image registration module is programmed to acquire an anatomical image of a heart using a first imaging modality, acquire a physiological image of the heart using a different second imaging modality, and identify a myocardium of a left ventricle using the physiological image. The image registration module is also programmed to automatically score a plurality of pixels in the anatomical image that are within a predetermined range of the myocardium identified in the physiological image, and register the anatomical image with the physiological image based on the score.

In a further embodiment, a computer readable medium encoded with a program to instruct a computer is provided. The computer readable medium is programmed to acquire an anatomical image of a heart using a first imaging modality, acquire a physiological image of the heart using a different second imaging modality, identify a myocardium of a left ventricle using the physiological image, automatically score a plurality of pixels in the anatomical image that are within a predetermined range of the myocardium identified in the physiological image, and register the anatomical image with the physiological image based on the score.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or multiple pieces of hardware). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

Figure 1:
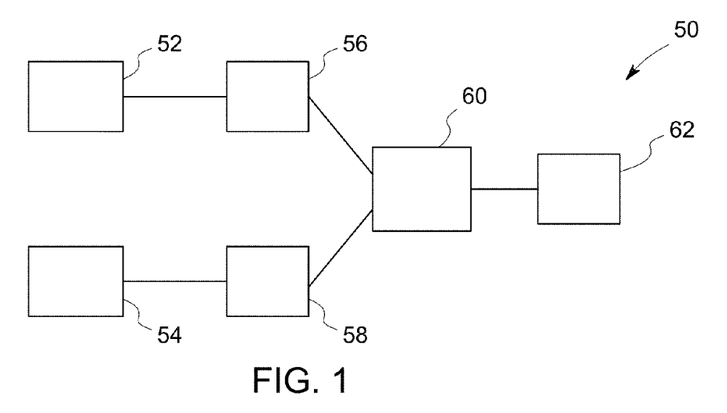
FIG. 1 is a schematic block diagram of an exemplary imaging system in accordance with various embodiments of the invention.

FIG. 1 is a schematic block diagram of an exemplary imaging system 50 formed in accordance with an embodiment of the present invention. In the exemplary embodiment, the imaging system 50 is a multi-modality imaging system that includes two different imaging modality units 52 and 54. The different imaging modalities may include a Positron Emission Tomography (PET), a Single Photon Emission Computed Tomography (SPECT), a Computed Tomography (CT), an ultrasound system, a Magnetic Resonance Imaging (MRI) or any other system capable or generating tomographic images. In some exemplary embodiments, the first modality unit 52 is a CT imaging system and the second modality unit 54 is one of a PET imaging system or a SPECT imaging system. It should be noted that the method according to various embodiments described herein may be used for registering a 3D anatomical image of a patient taken with a first single modality system such as a CT or MRI and a 3D physiological image of the same patient taken by a second single modality such as SPECT or PET.

During operation, the CT imaging system 52 is used to scan a patient to acquire sinogram data, referred to herein as a transmission data set 56 of an organ of interest. The transmission data set 56 is then used to reconstruct an anatomical or structural image of the organ of interest. In the exemplary embodiment, the transmission data set 56 is processed to reconstruct a three-dimensional (3D) image that corresponds to a plurality of two-dimensional (2D) slices taken through the organ of interest. In one embodiment, the 3D image may be reconstructed using a filtered back projection technique. The filtered backprojection technique converts the attenuation measurements from a scan into integers called "CT numbers" or "Hounsfield units", which are used to control the brightness of a corresponding pixel. The reconstructed slices are then combined to form the three-dimensional image of the organ of interest.

During operation, the PET or SPECT imaging system 54 identifies positrons that are emitted by radio nuclides previously injected into a patient and within the organ of interest. Hereinafter, in the interest of simplifying this explanation, an organ to be imaged including the left myocardium will be referred to generally as the "organ of interest" and the subject matter herein will be described with respect to the organ of interest. In PET studies. after the radiopharmaceutical becomes concentrated within the organ of interest and while the radionuclides decay, the radionuclides emit positrons. The positrons travel a very short distance before they encounter an electron and, when the positron encounters an electron, the positron is annihilated and converted into two photons, or gamma rays. The annihilation events are recorded by the PET imaging system 54 as an emission data set 58. The emission data set 58 is then used to reconstruct a physiological image of the organ of interest. The physiological image may be, for example, a perfusion or heart muscle viability image of the heart. Similarly, in SPECT studies, single photon emitting isotope or isotopes are used. The emission data set 58 is processed to reconstruct a three-dimensional (3D) image that corresponds to a plurality of two-dimensional (2D) slices taken through the same organ of interest.

As shown in FIG. 1, the imaging system 50 also includes an image registration module 60. The image registration module 60 as described herein is not limited to the multi-modality imaging system 50 shown in FIG. 1, but may be used on a single modality medical imaging system such as a stand-alone PET imaging system, a stand-alone SPECT imaging system, or a stand-alone CT imaging system.

During operation, the transmission data set 56 and the emission data set 58 output from the first and second modalites 52 and 54, respectively, is communicated to the image registration module 60. Optionally, the image registration module 60 may acquire 3D images from the first and second modalities 52 and 54. The transmission data set 56 and the emission data set 58 may be acquired in real time while the imaging system 50 is performing an imaging procedure. Optionally, the image registration module 60 may acquire stored medical data that was previously generated by the imaging system 50. The image registration module 60 is configured to utilize the transmission data set 56 and the emission data set 58, or images generated from the transmission data set 56 and the emission data set 58, to generate a registered image 62. In the exemplary embodiment, the registered image 62 represents a single image that includes a CT image overlayed with, and registered with, at least one of a SPECT image and a PET image.

Figure 2:
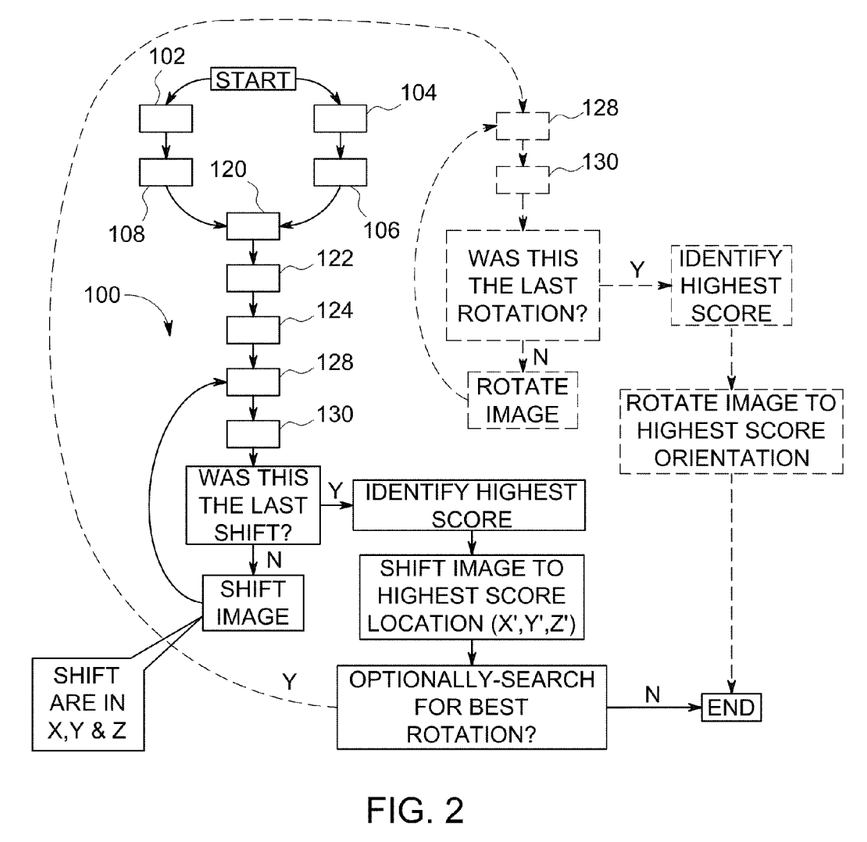
FIG. 2 is a flowchart of a method for registering images in accordance with various embodiments of the invention.

FIG. 2 is a block diagram of an exemplary method 100 for registering an anatomical image with a perfusion image. The method 100 may be performed by the image registration module 60 shown in FIG. 1. In the exemplary embodiment, the image registration module 60 is configured to register an anatomical image generated by the CT imaging system 52 with a SPECT or PET image generated by the imaging system 54. The method 100 may be applied to any image data set obtained using any of the imaging modalities discussed herein.

Referring again to FIG. 2, at 102, an anatomical image or an organ of interest is acquired using the CT imaging system 52. During operation, the CT imaging system 52 performs a scan to generate the transmission data set 56 discussed above. The transmission data set 56 is then used to reconstruct an image. To generate the image, a computer (not shown) or the image registration module 60 assigns each pixel in the image a CT number, represented as Hounsfield units, which may range, for example, between negative 1000 and positive 3000. Larger CT numbers are assigned to structures which creates greater attenuation. For example, a pixel representing air may be assigned a CT number of negative 1000 while a pixel representing water may be assigned a CT number of zero. Pixels representing bones with higher densities may be assigned a higher positive CT number than pixels representing soft tissue or bones with lower densities, comparatively. The CT numbers are then used to reconstruct an anatomical image of the object being scanned.

Figure 3:
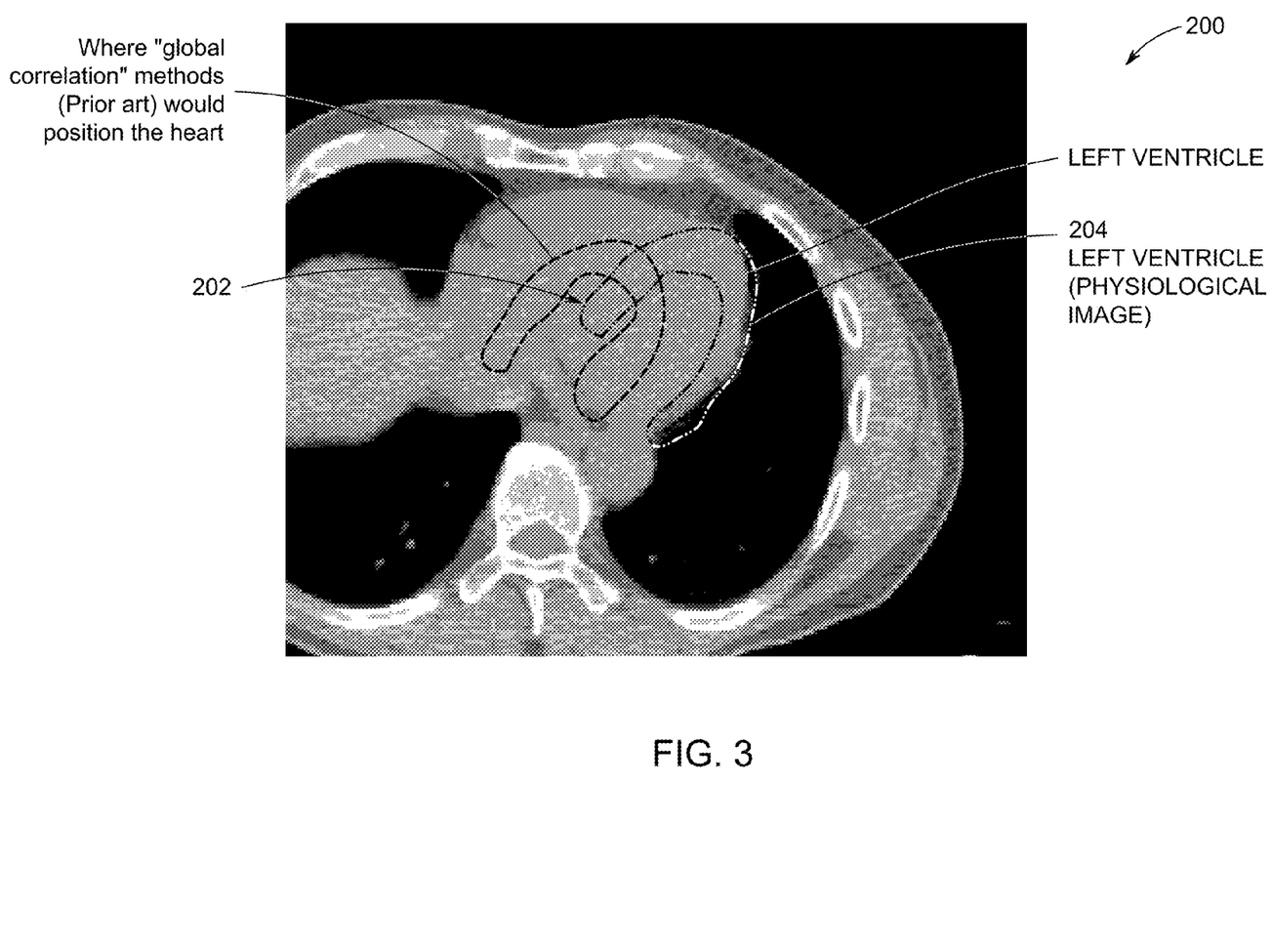
FIG. 3 is an exemplary image that is generated using the imaging system shown in FIG. 1 in accordance with various embodiments of the invention.

Many image reconstruction algorithms are currently implemented in commercially available CT systems and the image registration method 100 described herein may be implemented in connection with one or more such reconstruction algorithms. For example, the CT transmission data set 56 may be pre-processed, filtered and then backprojected to create the image. Alternatively, image data may have been previously acquired, and the raw, semi-processed, or processed data stored in a mass storage unit (not shown) for further image processing at a later time. FIG. 3 illustrates an exemplary anatomical image 200 that is generated using the CT transmission data set 56 (in gray levels, superimposed by a cut through the surface of the physiological reconstructed left myocardium). As shown in FIG. 3, the gray, white and black areas represent the structural elements of the organ being imaged. In this embodiment, the anatomical image 200 is a CT image of a human chest cavity illustrating the heart, the lungs, and the surrounding bone structures. It should be noted that order of 102 and 104 may be reversed.

At 104, a physiological image is acquired using the PET/SPECT imaging system 54. During operation, the PET/SPECT imaging system 54 performs a scan to generate the emission data set 58 discussed above. The emission data set 58 is then used to reconstruct a physiological image of the object being scanned. In the exemplary embodiment, the physiological image is segmented using a conventional method to define an outline 202 of the left ventricle myocardium also shown in FIG. 3. An exemplary method is disclosed for example in a paper titled "A New Algorithm for the Quantitation of Myocardial Perfusion SPECT"; to Guido Germano, et. al; published in the journal of nuclear medicine Vol. 41 No. 4 Apr. 2000. As shown in FIG. 3, which depicts one slice of each of the two 3D images, the outline 202 of the left ventricle myocardium overlayed onto the anatomical image 200. Also as shown in FIG. 3, the outline 202 of the left ventricle myocardium is not properly aligned with the anatomical image 200. In the exemplary embodiment, the method 100 utilizes the myocardium of the left ventricle to properly register and align the anatomical image 200 with the outline 202 of the left ventricle myocardium. As shown, prior to utilizing the image registration method 100 described herein, the myocardium of the left ventricle shown from the anatomical image 200 is not properly registered with the outline 202 of the myocardium of the left ventricle. Thus the anatomical image 200 in not properly registered or aligned with the perfusion image.

Figure 6:
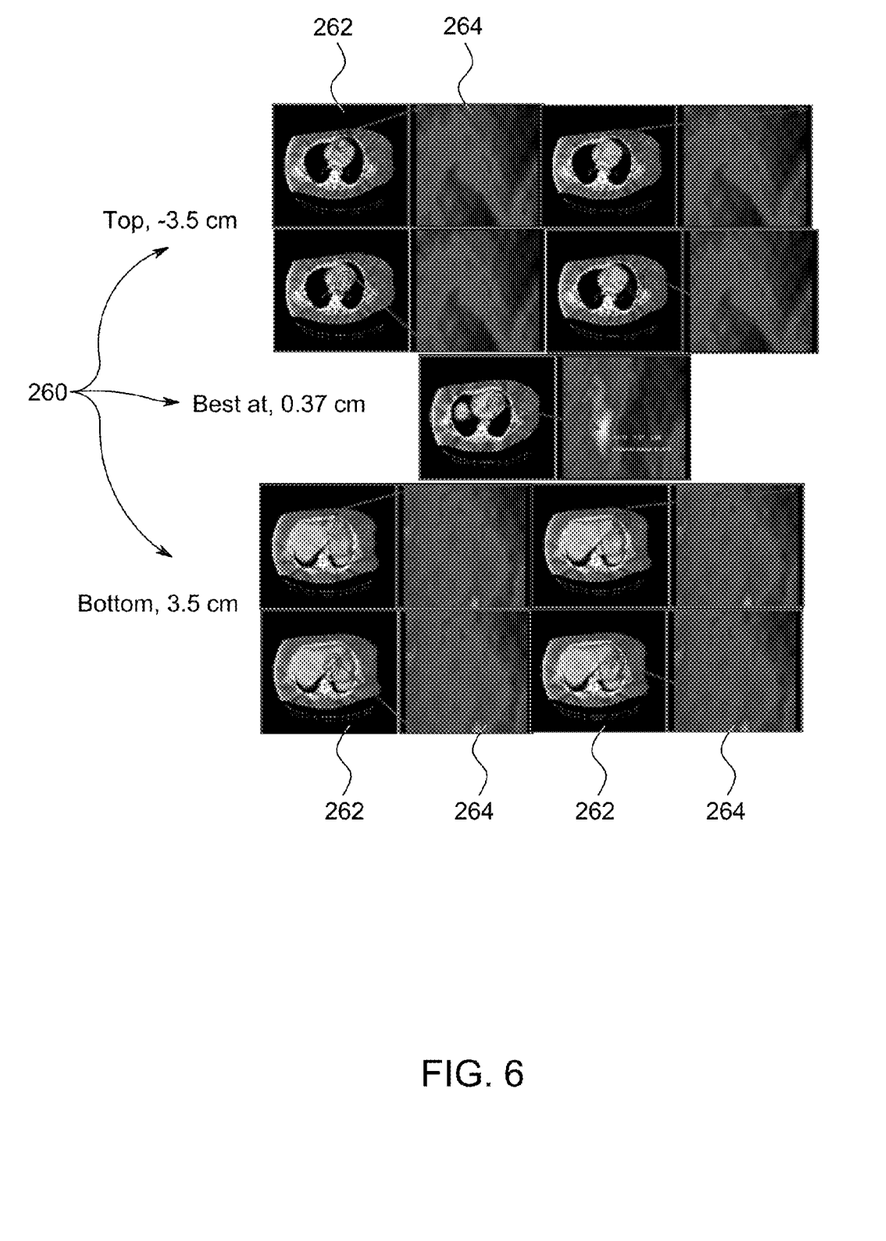
FIG. 6 illustrates a plurality of potential registration positions in accordance with various embodiments of the invention.

In the exemplary embodiment, the image registration module 60 is configured to automatically register the anatomical image 200 with an exemplary physiological image shown in FIG. 6, for example. More specifically, referring again to FIG. 2, at 106, the image registration module 60 is configured to identify an outer surface 204 of the myocardium of a left ventricle using the physiological image using a conventional segmentation technique.

Figure 4:
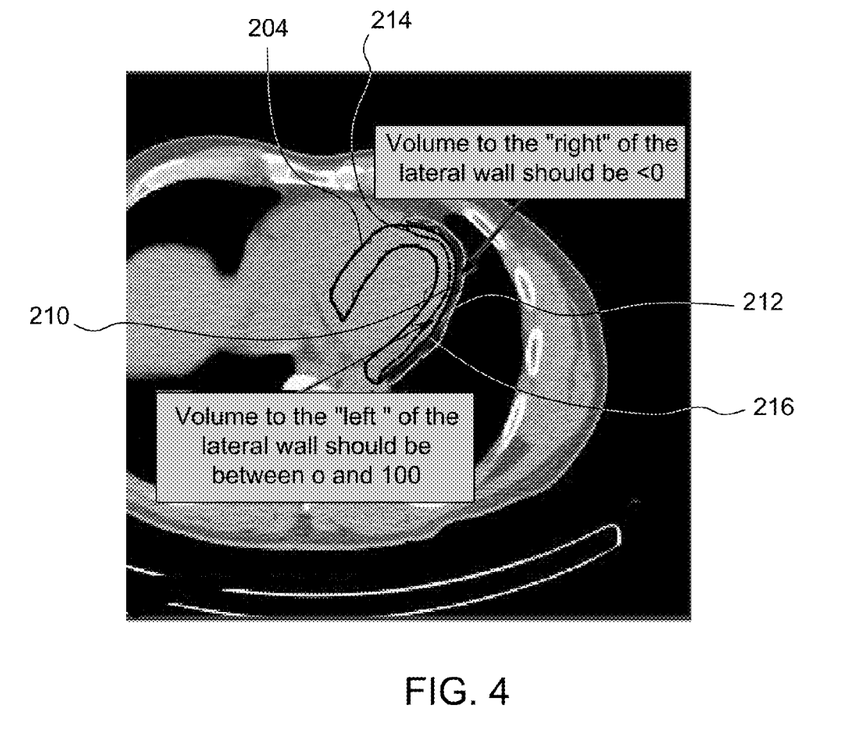
FIG. 4 illustrates exemplary boundaries defined by the image registration module shown in FIG. 1 in accordance with various embodiments of the invention.

At 108, the image registration module 60 is configured to automatically score a plurality of pixels within the anatomical image based on the outer surface 204 of the myocardium identified by the outline 202 of the left ventricle myocardium. More specifically, referring again to FIG. 2, to score the pixels in the anatomical image 200, at 120, the image registration module 60 utilizes the outline 202 of the left ventricle myocardium to identify a first boundary 210 and a second boundary 212 with respect to the outer surface of the myocardium determined at 106. For example, FIG. 4 illustrates the exemplary boundaries 210 and 212 defined by the image registration module 60. In the exemplary embodiment, the first boundary 210 (shown in green) is located to the left, or radially inward from the outer surface 204 of the left ventricle myocardium. The second boundary 212 (shown in red) is located to the right, or radially outward from the outer surface 204 of the left ventricle myocardium. The first and second boundaries 210 and 212 are located a predetermined distance from the outer surface 204. For example, the left and right boundaries 210 and 212 may be located in a range of between one and five pixels from the outer surface 204. The first and second boundaries 210 and 212 are located between two and three pixels from the outer surface 204. At 122, the image registration module 60 defines a first area 214 between the first boundary 210 and the outer left side surface 204. At 124, the image registration module defines a second area 216 between the second boundary 212 and the outer left side surface 204. After the boundaries 210 and 212 are determined, thus identifying the first and second area 214 and 216, the method 100 proceeds to 126.

Although FIG. 4 illustrates a single CT slice, it should be realized that the boundaries 210 and 212 are defined in three-dimensions. For example, assuming that the boundaries 210 and 212 are each selected to be three pixels from the outer surface 204, the boundaries 210 and 212 define a three-dimensional cube that is approximately seven pixels in an X-direction, seven pixels in a Y direction, and seven pixels in a Z direction. It should be realized that the outer surface 204 and the boundaries 210 and 212 are generated based on data in the physiological image discussed previously.

Figure 5:
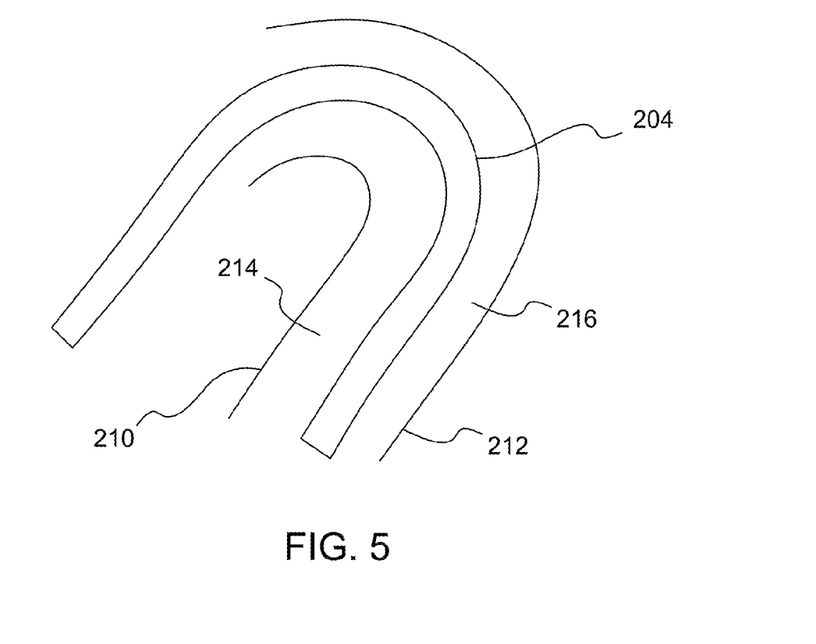
FIG. 5 illustrates an enlarged view of a portion of the heart shown in FIG. 4 in accordance with various embodiments of the invention.

Referring again to FIG. 2, at 126 pixels falling within each of the first and second areas 214 and 216 are identified as discussed below. At 128, a weight is assigned to each pixel identified in the first and second areas 214 and 216. For example, FIG. 5 illustrates an enlarged view of a portion of the heart shown in FIG. 4. The pixels within the anatomical image 200 that fall within the first area 214 defined in the physiological image are identified. Each pixel in the first area 214 is then assigned a weight that is based on the Hounsfield number or CT number of the pixel. For example, the first area 214 as shown in FIG. 5 is to the left of the outer surface 204. Therefore, in the exemplary embodiment, the pixels defined in the first area 214, for a properly registered image should be composed of mostly soft tissue, fluids, etc. Therefore, for a properly registered image, the pixels in the first area should have a CT number that is between approximately zero and approximately 100 Hounsfield units.

During operation, the image registration module 60 determines the CT numbers for each pixel in the first area 214. If a pixel in the first area 214 is greater than 0, e.g. the pixel count is 100, then a large weight, for example 1, is assigned to the pixel. If a pixel in the first area 214 has a pixel count that is less than 0, then a smaller weight is assigned to the pixel. In this manner, each pixel in the first area 214 is weighted based on whether the pixel is properly located in the first area 214, for example whether the pixel is soft tissue or air. In the exemplary embodiment, for a properly registered image, the majority of pixels in the first area 214 should have relatively high Hounsfield unit values and therefore should be assigned a relatively large weight indicating that the first area 214 is composed mostly of soft tissue and blood as is to be expected for a properly registered image. However, for an improperly registered image, many of the pixels in the first area 214 may have relatively low Hounsfield unit values and are therefore assigned a smaller weight indicating that many of the pixels represent air, for example. The weights of each pixel in the first area 214 are summed to generate a first partial score.

Additionally, the image registration module 60 determines the CT numbers for each pixel in the second area 216 (or on the surface of 212). As discussed above, for a properly registered image, the pixels in the second area 216 should be composed of mostly air. Therefore, for a properly registered image, the pixels in the second area 216 should have a CT number that is well below zero Hounsfield units. If a pixel in the second area 216 is less than 0 then a large weight, for example 1, is assigned to the pixel. If a pixel in the second area 216 is greater than zero, then a smaller weight is assigned to the pixel. In this manner, each pixel in the second area 216 is also weighted based on whether the pixel is properly located in the second area 216. In the exemplary embodiment, for a properly registered image, the majority of pixels in the second area 216 should be assigned a relatively large weight indicating that the second area 216 is composed mostly of air which is to be expected for a properly registered image. However, for an improperly registered image, many of the pixels in the second area 216 area may be assigned a smaller weight indicating that the pixel represents soft tissue or fluid, for example. The weights of each pixel in the second area 216 are summed to generate a second partial score.

At 130 the partial weights generated for both the first and second volumes 214 and 216 are summed over the entire 3D image to generate and save a summed score. Steps 126 to 130 are repeated for a plurality of relative shifts of boundaries 204, 210 and 212 over a predetermined range on the anatomical dataset 200 by testing 131 if the current shift exhausted the predetermined range. If the range, which is preferably defined in 3D, for example +/−3.5 cm in each of x, y and z directions was not yet exhausted, a new shifts for boundaries 204, 210 and 212 is selected 132 and new score is computed (steps 126, 128, 130).

The scores, each associated with a specific shift are thus stored in a 3D dataset. Several 2D slices of the 3D scoring dataset a depicted in the exemplary FIG. 6.

The highest score is identified 133, for example by a search through the entire scoring dataset and its associated shift is defined as the best match between the anatomical and physiological images.

Referring again to FIG. 2, at 110, the image registration module 60 is configured to automatically register the anatomical image with the physiological image based on the spatial summed scores determined at 133. The final score represents both the direction and quantity of registration required to properly register the anatomical image 200 and the physiological image. For example, for a properly registered image, the first boundary 210 should fall completely within the CT soft tissue region and the second boundary 212 should fall completely within the lung regions (the air region). Therefore, the pixels in each of the first and second volumes are weighted based on whether the pixels fall within the proper areas for a properly registered image. Based on the final score determined, the image registering module 60 is configured to automatically move the outline 202 of the left ventricle myocardium with respect to the anatomical image 200 to properly register the images. The highest or maximum final score is achieved when the anatomical image 200 is properly registered with the outline 202 of the left ventricle myocardium in all three directions. For example, FIG. 6 illustrates a plurality of potential registrations positions 260 wherein the left image 262 in each set is a potential registered image whereas the right image 264 in each set illustrates a visual indication of the total score calculated above. As shown in FIG. 6, the medium-to-dark shading represents pixels having a relatively low score. Whereas pixels having a relatively high score are illustrated using the lighter shading, e.g. the white shading.

In some instances, the anatomical image 200 may be grossly misaligned with the physiological image, for example separated by more than three pixels. In this case, the method 100 optionally may also include at 112 rotating or otherwise realigning at least one of the anatomical image 200 or the physiological image. The method 100 then proceeds back to 120. Rotating, or otherwise realigning, or optionally using an iterative process, at least one of the images enables the image registering module 60 to further refine the image registration process. Specifically, the image registration module is configured to rotate or shift the heart to improve the scores. After the maximum score is determined at a first location, the image registration module 60 shifts or rotates at least one of the images, as shown in FIG. 6, to determine a maxima score in a second location and thereby attempt to improve the final score and thus improve the final registration.

For example, referring again to FIG. 6, the image registration module 60 shifts the heart 3.5 centimeters to the right in an x-direction, 3.5 centimeters left in the x-direction, 3.5 centimeters front in a y-direction, 3.5 centimeters back in the y-direction, 3.5 centimeters up in a z-direction, and 3.5 centimeters down in the z-direction to optimize the 3D set of scores and thus optimize the final score. The final 3D score represents all the scores from the 2D slices. The center image 250 illustrates that the image registration module 60 has properly aligned the two images such that the majoring of the pixels have a relatively high score.

Figure 7:
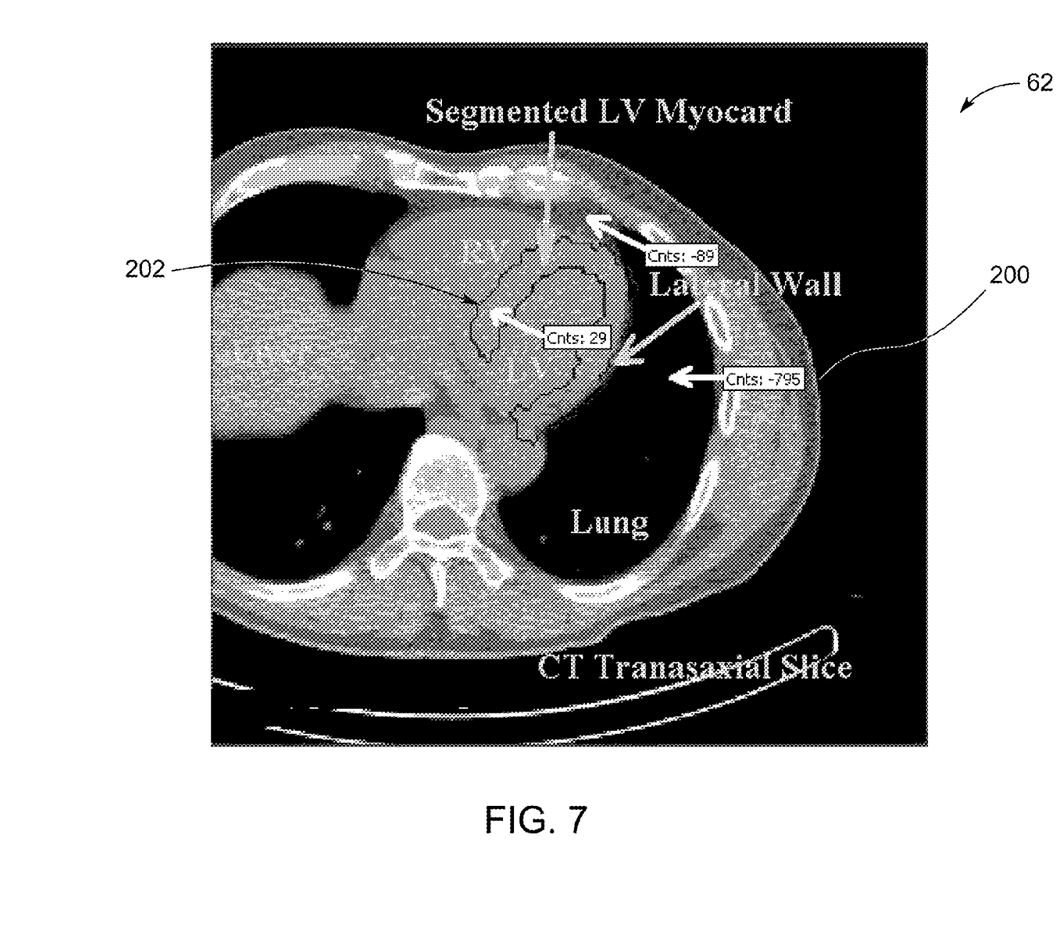
FIG. 7 illustrates a registered image formed in accordance with various embodiments of the invention.

FIG. 7 illustrates an exemplary registered image 62 wherein the anatomical image 200 is properly registered with the outline 202 of the left ventricle myocardium using the method 100 described herein.

In some embodiments, best registration is searched and obtained not only by shifting the anatomical and physiological images, but also in relative rotation of the two images with respect to one another. In these optional embodiments, when the user selects 135 to search for best relative rotation between the images, steps 126', 128', 130', 131', 132', 133' and 110' are executed wherein in these steps "shifting the boundaries" in 132 is replaced with "rotating the boundaries" in 132' and the predetermined range is defined over +/− range of few degrees in one, two or three axis of orientation.

It should be noted the method of searching for highest score by calculating the score for each and every shift (rotation) and searching for the highest calculated score value is exemplary only. Other methods of "maximum search" are known in the art and may be found for example in the book "numerical recopies".

It should be noted that the method according to the current invention which based on defining the "one sided" (to the right of the heart) boundaries and calculating the score for relative shifts (and optionally rotations) of the heart relative to the anatomical image ensures correct registration of the two images. This is in contrast to other registration methods of the art that uses "global correlation between two images". Methods of the art would often wrongly position the heart in the center of the gray soft tissue area as depicted by the centrally position outline 900 in FIG. 3.

A technical effect of the various embodiments describes herein is to automatically align two diagnostic images using data derived from both images. The method and apparatus are configured to identify the left ventricle in a perfusion image. Based on the location of the left ventricle first and second boundaries are identified. The boundaries are used to weight pixels in the anatomical image. Lower scores indicate that the images are not properly registered whereas higher scores indicate that the images are properly registered.

The various embodiments described herein perform both attenuation correction and quality control by applying automatic registration of multiple datasets based on the location of the myocardium of the left ventricle (LV). The registration may be used to perform attenuation correction of NM images using CT images, and/or to fuse anatomical images (CT Cardiac angiographic images) with physiological images (NM perfusion). During operation, the location of the left ventricle is determined by segmenting the perfusion image. The distribution of CT densities are then determined. The various embodiments utilize the information that the left myocardium is surrounded by a lung to the left and by soft tissue at other territories. The method processes the imaging data by moving and/or rotating the segmented LV all around the CT volume. The various embodiments sum the Hounsfield Units (HU) to the left of the LV accounting only for lung voxels, and also sum the Hounsfield Units (HU) to right account for soft tissues. In the presence of contrast agent in the CT image, additional weight is given to voxels within the LV blood pool in the NM space that falls over high HU values in the CT space. The methods described herein facilitate automatically registering diagnostic images acquired using a multi-modality imaging system. The methods compensate for one or some of: movement of the heart within the chest which is often observed after physical strain, table sag or patient movement, and also reduce the operator workload by reducing a time required to register images using manual registration techniques.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

Some embodiments of the embodiments described herein may be implemented on a machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for automatically registering an anatomical image with a physiological image, said method comprising:
    acquiring an anatomical image of a heart using a first imaging modality;
    acquiring a physiological image of the heart using a different second imaging modality apparatus;
    identifying, by a module, a myocardium of a left ventricle using the physiological image;
    defining, by a module, an outer surface of the left ventricle using a perfusion image;
    automatically scoring, by a module, a plurality of pixels in the anatomical image that are within a predetermined distance of the outer surface of the left ventricle myocardium identified in the physiological image; and
    registering, by a module, the anatomical image with the physiological image based on the score.

2. The method of claim 1 wherein the scoring further comprises:
    defining a first area between an outer surface of the left ventricle myocardium and a first boundary using a perfusion image;
    defining a second area between the outer surface of the left ventricle myocardium and a second boundary using the perfusion image; and
    scoring the pixels in the anatomical image that are within the first and second areas.

3. The method of claim of 1 wherein the scoring further comprises:
    determining the Hounsfield units for each of the plurality of pixels within the predetermined range; and
    summing the Hounsfield units to generate the score.

4. The method of claim 1 further comprising:
    determining the Hounsfield units for each of the plurality of pixels within the predetermined range; and
    weighting the pixels based on the Hounsfield units to generate the score.

5. The method of claim 1 further comprising segmenting the physiological image to identify the myocardium of the left ventricle.

6. The method of claim 1 further comprising:
    acquiring an anatomical image of a heart using a computed tomography imaging system; and
    acquiring a physiological image of the heart using at least one of a Positron Emission Tomography (PET) and a Single Photon Emission Computed Tomography (SPECT) imaging system.

7. The method of claim 1 further comprising:
    assigning a first score to each pixel in the anatomical image that is disposed on a first side of the myocardium of the left ventricle based on each pixel's CT number;
    assigning a second score to each pixel in the anatomical image that is disposed on an opposite side of the myocardium of the left ventricle based on each pixels CT number; and
    combining the scores to determine a direction and quantity to shift the anatomical image with respect to the physiological image.

8. The method of claim 1 further comprising rotating or shifting at least one of the physiological image and the anatomical image prior to scoring the pixels in the anatomical image.

9. A multi-modality imaging system comprising a first imaging modality apparatus, a second imaging modality apparatus, and an image registration module operationally coupled to the first and second imaging modality apparatuses, wherein the image registration module is programmed to:
- acquire an anatomical image of a heart using the first imaging modality apparatus;
- acquire a physiological image of the heart using the second imaging modality apparatus, which is different from the first imaging modality apparatus;
- identify a myocardium of a left ventricle using the physiological image;
- define an outer surface of the left ventricle using a perfusion image;
- automatically score a plurality of pixels in the anatomical image that are within a predetermined distance of the outer surface of the left ventricle myocardium identified in the physiological image; and
- register the anatomical image with the physiological image based on the score.

10. A multi-modality imaging system in accordance with claim 9, wherein the physiological image is a perfusion image, wherein the image registration module is further programmed to:
- define a first area between the outer surface of the left ventricle myocardium and a first boundary using the perfusion image;
- define a second area between the outer surface of the left ventricle myocardium and a second boundary using the perfusion image; and
- score the pixels in the anatomical image that are within the first and second areas based on the pixels Hounsfield numbers.

11. A multi-modality imaging system in accordance with claim 9, wherein the image registration module is further programmed to:
- determine the Hounsfield units for each of the plurality of pixels within the predetermined range; and
- sum the Hounsfield units to generate the score.

12. A multi-modality imaging system in accordance with claim 9, wherein the image registration module is further programmed to:
- determine the Hounsfield units for each of the plurality of pixels within the predetermined range; and
- weight the pixels based on the Hounsfield units to generate the score.

13. A multi-modality imaging system in accordance with claim 9, wherein the image registration module is further programmed to:
- assign a first score to each pixel in the anatomical image that is disposed on a first side of the myocardium of the left ventricle based on each pixel's CT number;
- assign a second score to each pixel in the anatomical image that is disposed on an opposite side of the myocardium of the left ventricle based on each pixels CT number; and
- combine the scores to determine a direction and quantity to shift the anatomical image with respect to the physiological image.

14. A multi-modality imaging system in accordance with claim 9, wherein the image registration module is further programmed to rotate or shift at least one of the physiological image and the anatomical image prior to scoring the pixels in the anatomical image.

15. A non-transitory computer-readable medium encoded with a program to instruct a computer to:
- acquire an anatomical image of a heart using a first imaging modality;
- acquire a physiological image of the heart using a different second imaging modality;
- identify a myocardium of a left ventricle using the physiological image;
- define an outer surface of the left ventricle left myocardium using a perfusion image;
- automatically score a plurality of pixels in the anatomical image that are within a predetermined distance of the outer surface of the left ventricle myocardium identified in the physiological image; and
- register the anatomical image with the physiological image based on the score.

16. A non-transitory computer-readable medium in accordance with claim 15 wherein the program is programmed to further instruct a computer to:
- define a first area between the outer surface of the left ventricle myocardium and a first boundary using a perfusion image;
- define a second area between the outer surface of the left ventricle myocardium and a second boundary using the perfusion image; and
- score the pixels in the anatomical image that are within the first and second areas based on the pixels Hounsfield numbers.

17. A non-transitory computer-readable medium in accordance with claim 15 wherein the program is programmed to further instruct a computer to:
- determine the Hounsfield units for each of the plurality of pixels within the predetermined range; and
- sum the Hounsfield units to generate the score.

18. A non-transitory computer-readable medium in accordance with claim 15 wherein the program is programmed to further instruct a computer to:
- determine the Hounsfield units for each of the plurality of pixels within the predetermined range; and
- weight the pixels based on the Hounsfield units to generate the score.

19. A non-transitory computer-readable medium in accordance with claim 15 wherein the program is programmed to further instruct a computer to:
- assign a first score to each pixel in the anatomical image that is disposed on a first side of the myocardium of the left ventricle based on each pixel's CT number;
- assign a second score to each pixel in the anatomical image that is disposed on an opposite side of the myocardium of the left ventricle based on each pixels CT number; and
- combine the scores to determine a direction and quantity to shift the anatomical image with respect to the physiological image.

* * * * *